United States Patent [19]

Porter et al.

[11] 4,350,834
[45] Sep. 21, 1982

[54] VINYL CYCLOPROPYL COMPOUNDS AS PRECURSORS TO FATTY ACID OXIDATION PRODUCTS

[75] Inventors: Ned A. Porter; Carl B. Ziegler, Jr.; David H. Roberts, all of Durham, N.C.

[73] Assignee: Duke University, Durham, N.C.

[21] Appl. No.: 181,833

[22] Filed: Aug. 27, 1980

[51] Int. Cl.³ .............................................. C07C 179/02
[52] U.S. Cl. .................................. 568/568; 260/405.5; 260/410; 260/410.9 R; 560/147; 568/564; 562/512
[58] Field of Search ................ 568/568, 569, 571, 564, 568/578; 260/410.9 R, 410.9 N, 413, 405.5; 562/512, 598; 560/147

[56] References Cited

U.S. PATENT DOCUMENTS

| | | | |
|---|---|---|---|
| 2,430,865 | 11/1947 | Farkas et al. | 568/568 |
| 2,573,947 | 11/1951 | Bell | 568/568 |
| 3,308,163 | 5/1967 | McKellin | 568/568 |
| 3,751,477 | 8/1973 | Roberts | 568/571 |

OTHER PUBLICATIONS

Corey et al., "J. Amer. Chem. Soc." vol. 100, p. 1942 (1980).
Corey et al., "J. Amer. Chem. Soc.", vol. 102, p. 1435 (1980).
Porter et al., "J. Org. Chem.", vol. 44, p. 3177 (1979).

*Primary Examiner*—Werren B. Lone
*Attorney, Agent, or Firm*—Oblon, Fisher, Spivak, McClelland & Maier

[57] ABSTRACT

A nucleophile substituted unsaturated hydrocarbon based compound is prepared by reacting a compound of the formula:

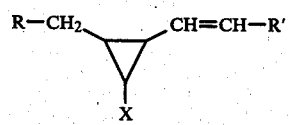

wherein R and R' are hydrogen, alkyl, alkenyl, cycloalkyl, cycloalkenyl, aryl, aralkyl, alkoxyalkyl, alkoxy, alkylthioalkyl, or carboxyalkyl or carboxyalkenyl and X is a leaving group selected from the group consisting of chlorine, bromine, and iodine with a nucleophilic reagent.

9 Claims, No Drawings

VINYL CYCLOPROPYL COMPOUNDS AS PRECURSORS TO FATTY ACID OXIDATION PRODUCTS

ACKNOWLEDGEMENT

Part of the invention was made under financial support of the National Institute of Health.

BACKGROUND OF THE INVENTION

1. Field of the Invention

The present invention relates to a method and reagent for the opening of the cyclopropyl ring of vinyl cyclopropyl compounds with the simultaneous introduction of a nucleophile into the product compound. More particularly, the present invention relates to a method of converting unsaturated fatty acids containing a vinyl cyclopropyl structure to a hydroxy or hydroperoxy fatty acid.

2. Description of the Prior Art

Both the hydroxy and hydroperoxy derivatives of certain fatty acids conventionally formed by the action of lipoxygenase enzymes on various acid substrates are of medical interest because it is believed that they play significant roles in platelet pharmacology and in the inflammation of various tissues. For example, 12-L-hydroxy-5,8,10,14-eicosatetraenoic acid exhibits chemotatic activity of neutrophils. The corresponding hydroperoxy derivative as well as other hydroperoxy positional isomers modulate the enzymes that control prostaglandin metabolism. E. J. Corey et al, *J.Am.Chem. Soc.*, 100, 1942(1978) recently have described a total synthesis of this compound.

Recently, two previously unknown monohydroxy $C_{20}$ fatty acids, 5-L-hydroxy-6,8,11,14-eicosatetraenoic acid, whose chemical and enzymatic synthesis has recently been reported by E. J. Corey et al *J. Am.Chem. Soc.*, 102, 1435(1980), and 8-L-hydroxy-9,11,14-eicosatetraenoic acid, have been isolated from rabbit neutrophils. The structure of these compounds which contains a cis, trans conjugated diene unit suggests that the monohydroxy acid compounds are probably formed from the corresponding intermediate hydroperoxy compounds. In fact, it has been demonstrated that the hydroxy group of 5-L-hydroxy-6,8,11,14-eicosatetraenoic acid is derived from molecular oxygen which is a finding consistent with the intermediacy of the corresponding hydroperoxy compound.

Interest in all of the above-discussed compounds as well as their hydroperoxy intermediates has also been heightened by the postulate that 5-L-hydroperoxy-6,8,11,14-eicosatetraenoic acid is a key intermediate in the biosynthesis of leukotrienes. One member of this important group of compounds is leukotriene C, which is the slow reacting substance of anaphylaxis, which causes prolonged smooth muscle contraction that is not inhibited by conventional anti-histamines. Leukotriene C is also believed to be intimately involved in the allergic response and may very well be an important factor in certain types of asthma. Samuelsson et al (*Proc.Nat. Acad.Sci*, 76, 4275 (1979)) has suggested that leukotriene C is biochemically prepared by a series of reactions in which 5-L-hydroperoxy-6,8,11,14-eicosatetraenoic acid (an arachidonic acid hydroperoxide) is converted to leukotriene A, which is an epoxide. Leukotriene A is then converted to leukotriene C by reaction with the cysteine sulfur nucleophile. Even though the above suggested synthetic scheme has not been unequivocally established, nevertheless the fundamentally important function which the arachidonic acid hydroperoxide derivatives exhibit in inflammation and in certain forms of asthma is gaining increased recognition by the scientific community.

In view of the above developments there is an obvious need for a study of the oxidative metabolism of unsaturated fatty acid compounds. The oxidation products (endoperoxides and hydroperoxides) are evidently important factors in such major traumatic events as the inflammation process, blood platelet aggregation and consequently heart attack and stroke and the allergic response. Studies, therefore, directed to an understanding of the fundamental chemistry involved in fatty acid oxidation are believed to be important to a proper understanding of these pathological conditions. Previous attempts at synthesizing various hydroxy and hydroperoxy derivatives of various unsaturated compounds have been limited to enzyme catalyzed oxidation reactions of unsaturated fatty acids and suh nonenzymatic reactions as the reaction of singlet oxygen generated by photolysis of molecular oxygen with the likes of arachidonic acid. (Porter et al, *J.Org.Chem.*, 44, 3177 (1979)). Another proposed method of synthesis involves the autooxidation of arachidonic acid. However, in both known non-enzymatic oxidation reactions, a complex mixture of product compounds is obtained in low yield which requires tedious chromatographic separation. A need, therefore, continues to exist for a method by which unsaturated fatty acid substrates can be oxidized to just a few, rather than a broad spectrum of possible corresponding hydroperoxy and hydroxy derivatives in good yield.

SUMMARY OF THE INVENTION

Accordingly, one objective of the present invention is to provide a method by which unsaturated fatty acid compounds can be oxidatively converted by a nonenzymatic process to a selectively narrow spectrum of hydroperoxy and hydroxy derivatives in good yield.

Another object of the present invention is to provide a method by which hydroperoxy functionality can be introduced into an unsaturated hydrocarbon compound. Yet another object of the invention is to provide hydroperoxy and peroxy derivatives of unsaturated fatty acid compounds for a study of the role of these derivatives in several pathological conditions relating to the allergic response, inflammation and blood platelet aggregation.

Briefly, these objects and other objects of the present invention as hereinafter will become more readily apparent can be attained by a method for synthesizing a nucleophile substituted unsaturated hydrocarbon based compound by reacting a compound of the formula:

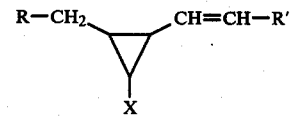

wherein R and R' independently are hydrogen, alkyl, alkenyl, cycloalkyl, cycloalkenyl, aryl, aralkyl, alkoxyalkyl, alkoxy, alkylthioalkyl, carboxyalkyl, or carboxyalkenyl, and X is a leaving group selected from the group consisting of chlorine, bromine and iodine, with a nucleophilic reagent.

DETAILED DESCRIPTION OF THE PREFERRED EMBODIMENTS

The central feature of the present invention is based upon the discovery that when a vinyl cyclopropyl compound bearing an appropriate leaving substituent is reacted with a nucleophile, the cyclopropyl ring is opened with the attachment of the nucleophile to a portion of the molecule. When the cyclopropyl ring is opened, a new olefinic bond is formed within the molecule which is conjugate to the olefinic bond of the vinyl group or an olefinic bond derived from the vinyl group. The key feature of the reactive vinylcyclopropyl substrate of the present invention is the attachment of a vinyl group on the cyclopropyl ring and the presence of a leaving group at one of the other two carbon atoms of the cyclopropyl ring.

The vinyl cyclopropyl compound employed in the present invention has the formula:

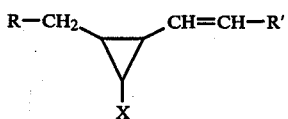

wherein sustituents R and R' are hydrogen, alkyl of four to ten carbon atoms, alkenyl of four to ten carbon atoms containing at least one site of unsaturation, cycloalkyl, cycloalkenyl, aryl, aralkyl, alkoxyalkyl, alkoxy, alkylthioalkyl, carboxyalkyl, carboxyalkenyl, or the like.

Suitable specific examples of substituents include methyl, ethyl, propyl, butyl, hexyl, vinyl, propenyl, butenyl, hexenyl, cyclopentyl, cyclohexyl, cyclohexenyl, phenyl, naphthyl, benzyl, phenethyl and the like.

Suitable leaving substituents (X) include bromo, chloro, iodo, and the like.

The nucleophile which reacts with the vinylcyclopropyl substrate can be any nucleophile which will attack the cyclopropyl ring of the substrate or the vinyl group or an olefinic group conjugate to the vinyl group and bond to the site which it attacks and causes the opening of the cyclopropyl ring with the elimination of the leaving group (X) and formation of an olefinic bond in conjugation with the olefinic bond of the vinyl group or olefinic group derived from the vinyl group. Suitable nucleophilic agents which can react with the vinylcyclopropyl compound include amines, organosulfides, organohydroperoxides, alkoxides, and the like. An especially preferred nucleophile is a Ag+ salt/$H_2O_2$ mixture which permits the introduction of a hydroperoxy substituent in the product compound. Suitable silver salts include the likes of silver nitrate, silver sulfate, silver trifluoroacetate, and the like.

The cyclopropyl ring opening reaction can be simply conducted by reacting the vinylcyclopropyl compound with the nucleophilic reagent under nonstrenuous conditions. Thus, the reaction can be conducted at temperatures ranging from 0° to 40° C. in a solvent which dissolves the vinylcyclopropyl compound and facilitates the reaction of the nucleophilic reagent with the vinylcyclopropyl compound. Suitable solvents include dialkyl ether compounds such as diethylether, dipropylether; dialkylformamide compounds such as dimethylformamide; acetonitrile; trifluoroethanol; dimethylsulfoxide and the like. The amounts of vinylcyclopropyl compound and nucleophilic reagent employed in the reaction are not critical with the only objective being to conduct the reaction as far as possible to completion. Accordingly, the amount of nucleophilic reagent reacted with the vinylcyclopropyl compound can range from one to one hundred moles of nucleophilic reagent per mole of vinylcyclopropyl compound.

In a preferred embodiment of the present invention a fatty acid derivative containing a vinyl cyclopropyl structure of the formula:

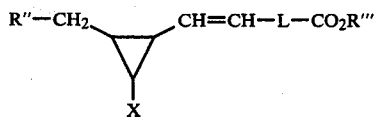

is reacted with a nucleophilic reagent. A preferred nucleophilic reagent in the reaction is Ag+ salt/$H_2O_2$ mixture which introduces a hydroperoxy substituent in the product. Accordingly, the use of this particular nucleophilic reagent permits the synthesis of an important group of hydroperoxy and hydroxy substituted unsaturated fatty acids or esters thereof which are found in biological systems. The hydroperoxy group can also be introduced into the product molecule by using an organohydroperoxide of the formula ROOH, wherein R is an alkyl or aryl radical, in place of hydrogen peroxide in the above mentioned nucleophilic reagent. The product of the reaction will contain an organoperoxy group from which the R radical can be removed and replaced by hydrogen by conventional reaction methodology.

In the above formula of the unsaturated acid or ester derivative, suitable R'' substituents include hydrogen; alkyl such as methyl, ethyl, pentyl, hexyl and the like; alkenyl containing at least one olefinic site such as vinyl, propenyl, butenyl, hexenyl, heptenyl, $CH_3(CH_2)_4$—CH=CH—, $CH_3(CH_2)_4CH$=CH—$CH_2$—CH=CH—, and the like, aralkyl and aralkenyl containing at least one olefinic site such as phenylvinyl, phenylpropenyl and the like. Suitable L substituents include alkylene of three to nine carbon atoms; alkylene of three to nine carbon atoms containing at least one olefinic group such as —$CH_2CH$=$CHCH_2CH$=$CH(CH_2)_3$—, —$CH_2CH$=CH—$(CH_2)_3$—, and the like. Suitable R''' substituents include hydrogen and alkyl such as methyl, ethyl, butyl, pentyl, and the like; aryl; aralkyl; and the like. The leaving group X is the same as defined above.

Another embodiment of the vinylcyclopropyl group containing fatty acid or ester compounds of the present invention includes compounds of the formula:

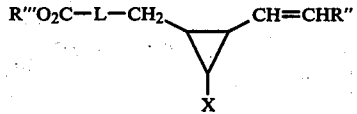

wherein R', R''', L and X are as defined above.

In addition to the nucleophilic reagent described above for the introduction of the hydroperoxy substituent in the fatty acid molecule, other nucleophilic reagents can be used as described earlier depending upon the type of substituted fatty acid product desired. The conditions employed for the synthesis of the hydroperoxy or hydroxy substituted fatty acid product are the same as those described above.

If it is desired to reduce the hydroperoxy group in the product fatty acid or ester molecule to the corresponding hydroxy group, this can be done with the use of an appropriate reducing agent by conventional reaction methodology. Suitable reducing agents include triarylphosphines such as triphenylphosphine trialkylphosphites, mercaptans, organosulfides and the like.

The utility of the method of the present invention is that it provides a relatively simple way of synthesizing compounds which have been shown or are suspected to possess significant biological properties relating to inflammation, the allergic response and blood platelet aggregation. The present invention also provides a general synthetic technique by which a cyclopropyl ring within a molecule can be opened to introduce another olefinic bond into the molecule while also introducing a substituent in the molecule.

Having generally described the invention, a further understanding can be obtained by reference to certain specific examples which are provided herein for purpose of illustration only and are not intended to be limiting unless otherwise specified.

EXAMPLE 1

2-Hydroperoxy-3,5-heptadiene

To a 5 ml round bottom flask are added 4 mg (0.023 mmoles) 2-bromo-3-(1-propenyl) methylcyclopropane, 270 μl 1 anhydrous ether and 270 μl 90% HOOH (450 equivalents). In one addition, 510 mg silver trifluoroacetate (100 equivalents) are added and the solution is stirred at room temperature for 15 minutes. The reaction is diluted with 15 ml ether, washed once with 10 ml saturated NaHCO$_3$, and once with 10 ml saturated NaCl solution, then dried over MgSO$_4$. After filtration, the product hydroperoxides are either converted to their corresponding alcohols or are concentrated on a rotovaporator and purified by chromatography (Water's μ porasil, 15% EtOAc/hexane).

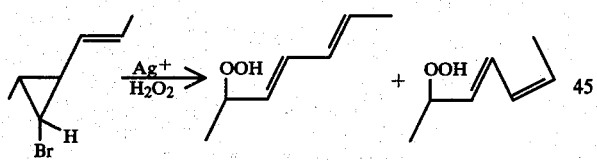

The hydroperoxides obtained were reduced to the corresponding hydroxy compounds as follows:

2-Hydroxy-3,5-heptadiene

To a 25 ml round bottom flask is added the crude 15 ml ether solution containing the product hydroperoxides. A few drops of water are added to 'wet' the ether followed by approximately 100 mg triphenyl phosphine. The solution is stirred at room temperature for 15 minutes then dried over MgSO$_4$. After filtration, the solution is concentrated to approximately 1 ml for capillary GC analysis. The hydroxy products obtained compared favorably with authentic samples of the alcohol products.

The following reactions were conducted in the manner described above and show the types of products obtained as a function of the structure of the vinyl cyclopropyl bromide compound used.

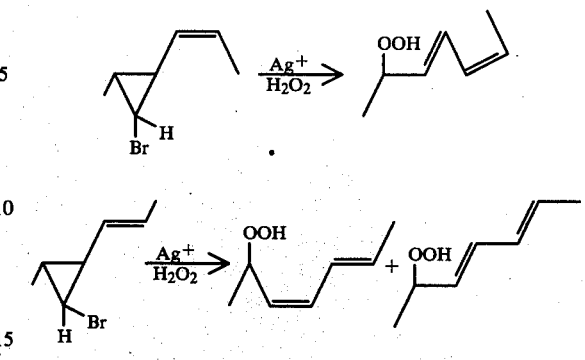

EXAMPLE 2

The following is the series of reactions employed to prepare the hydroperoxy compounds shown below.

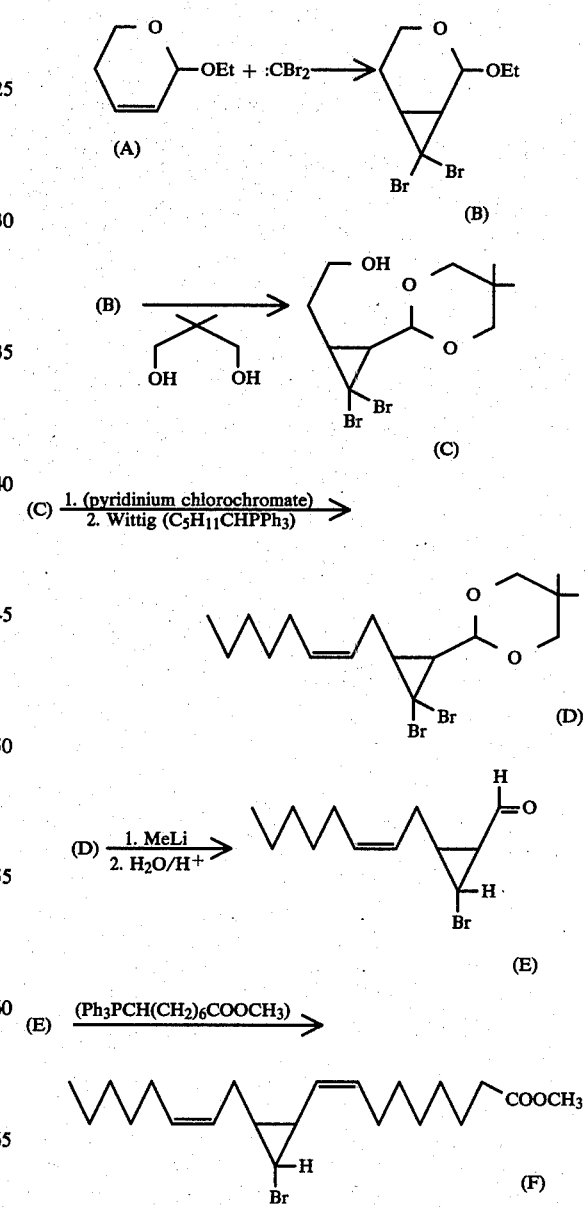

(F) 

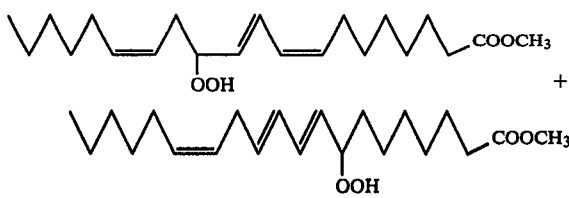

Synthesis of Compound (B)

A mixture containing 32.4 gm (0.253 mol) of compound A 128 mg (0.506 mol) CHBr₃ in a solvent system containing 56 ml CH₂Cl₂, 90 ml 50% NaOH and 10 ml tetrabutylammonium hydroxide was stirred at 42° C. After 20 hr the reaction was stopped and the entire reaction contents were extracted with petroleum ether for 24 hr in a liquid-liquid continuous extractor. The petroleum ether solution was then washed several times with NH₄Cl solution and with water. The organic solution was dried (MgSO₄) and then the solvent removed. The excess CHBr₃ was separated from the product by distillation (40°-50°/0.1 mm) leaving a yellow oil weighing 40 gm (52%). The product could be further purified by column chromatography on Florisil, eluting with 2% Et₂O/98% C₆H₁₄. The dibromide (B) was thermally unstable and could not be distilled.

Synthesis of alcohol C

A solution containing 0.5 gm (2.0 mmol) dibromide (B) 2.0 gm (19.2 mmol) 2,2-dimethylpropandiol and a catalytic amount of toluenesulfonic acid in 9 ml of benzene was refluxed under a N₂ atmosphere. After four hr no starting material remained and the reaction was diluted with 25 ml benzene, washed with saturated NaHCO₃ solution and then three times with water and finally dried (MgSO₄). The products were purified via column chromatography on Florisil, eluting with 15% Et₂O/85% C₆H₁₄. C(398 mg, 55%) was the most polar product.

Oxidation of compound C to the aldehyde 2.28 gm (6.37 mmol) (C) was oxidized with pyridinium chlorochromate at 15° C. The reaction progress was monitored by TLC. After ten hr reaction time all of (C) had been consumed. The crude product, an oil weighing 1.72 gm (75%), crystallized from Et₂O. The colorless solid (85° dec.) slowly decomposes at room temperature.

Synthesis of acetal D n-Hexyl-triphenylphosphonium bromide, 7.26 gm (17 mmol), was suspended in 52 ml of freshly distilled THF under a N₂ atmosphere at −20° C. To this was added dropwise 7.0 ml of a 2.4 M (16.8 mmol) solution of n-butyllithium. The resulting orange colored ylid was stirred at −20° C. for 20 min, then the temperature was raised to 0°-5° C. To this ylid solution was added dropwise 1.52 gm (4.25 mmol) aldehyde dissolved in 8.5 ml dry THF. The resulting solution was then stirred for 2.25 hr at 0°-5° C. and then quenched by the addition of 8 ml cold H₂O. The reaction mixture was diluted with 65 ml Et₂O and washed with brine and then water. The organic solution was dried (MgSO₄). The solvent was removed leaving an oil which was purified via cold column chromatography (−10° C.) on Florisil and 1% Et₂O/99% C₆H₁₄ eluant. The product D weighed 1.29 gm (71%).

Reaction of Compound D with methyl lithium 1.29 gm (3.04 mmole) D in 30 ml ether was cooled to −78° C. and to this solution was added 8 mmol methyllithium-lithium bromide over 4 min. The mixture was stirred for 20 min and quenched by the slow addition of 1 ml of water. The monobromide acetal was purified by cold column chromatography (−10° C.) eluting with 1% ether, 99% hexane. Yield: 0.836 gm (80%).

Synthesis of Compound E

A solution containing 96 mg (0.28 mmol) monobromide acetal in 0.5 ml THF and 3.5 ml of 88% formic acid were stirred at 0° under a N₂ atmosphere for 31 hr. At this time, all of the monobromide acetal was consumed. A mix of cold brine and ether was added to the reaction. The organic layer was washed three times with brine and then neutralized with saturated bicarbonate solution. The organic solution was dried (MgSO₄) and kept cold. Purification via cold column chromatography (−10° C.) on Florisil with 4% Et₂O/96% C₆H₁₄ eluent yielded 64 mg (88%) aldehyde (E). The aldehyde slowly decomposes at room temperature and should be stored at −20° C.

Synthesis of Wittig Product F

The phosphonium salt 0.370 gm (0.74 mmol) that was previously dried at 100° C./0.1 mm was dissolved in 3.5 ml of freshly distilled THF at room temperature and under a N₂ atmosphere. To this was added dropwise 1.4 ml (0.70 mmol) of 0.5 M THF solution of potassium t-butoxide. The resulting ylid solution was stirred at room temperature for 15 min and then the temperature was lowered to 0°. A solution containing 1.6 ml dry THF and 63 mg (0.24 mmol) aldehyde was added dropwise. The resulting solution was stirred at 0° for three hr. The reaction was quenched by the dropwise addition of 1 ml cold H₂O followed by addition of a cold brine and ether mixture. The organic phase was dried (MgSO₄) and the solvent removed leaving an oil. The product was purified via cold column chromatography (−10° C.) on Florisil, eluting with 4% Et₂O/96% C₆H₁₄. The purified product 82 mg (85%) was not stable at room temperature for periods longer than a few hours.

Reaction of Compound F with Ag+/H₂O₂

In 6.6 ml of dry ethyl ether at 0° C. was dissolved 40 mg (0.1 mmol) bromide (F). To this solution was added 0.95 ml 90% H₂O₂ (36.3 mmol) in one portion. The solution of F and H₂O₂ was allowed to warm to slightly below room temperature and then 0.758 gm (3.5 mmol) of silver trifluoroacetate was added in one portion. A yellowish precipitate of AgBr formed almost immediately. The reaction was allowed to stir for five to ten min and then was quenched by the addition of a cold mixture of aqueous NaHCO₃ and ether. The ether solution was washed twice with the bicarbonate and then dried (MgSO₄). The products were purified via cold column chromatography (−10°) on Florisil eluting with 15% Et₂O/85% C₆H₁₄. The two products isolated 25 mg (71%) gave a positive peroxide test to a ferrous thiocyanate spray reagent on TLC (silica gel plates, 50% Et₂O/50% C₆H₁₄). The two products had identi-

Having now fully described the invention, it will be apparent to one of ordinary skill in the art that many changes and modifications can be made thereto without departing from the spirit or scope of the invention as set forth herein.

What is claimed as new and is intended to be secured by Letters Patent is:

1. A method of synthesizing a nucleophile substituted unsaturated hydrocarbon based compound comprising: reacting a compound of the formula:

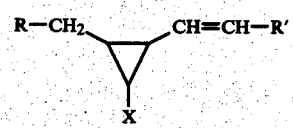

wherein R and R' are hydrogen, alkyl, alkenyl, cycloalkyl, cycloalkenyl, aryl, aralkyl, alkoxyalkyl, alkoxy, alkylthioalkyl, carboxyalkyl, carboxyalkenyl, and X is a leaving group selected from the group consisting of chlorine, bromine, and iodine with a nucleophilic $Ag^+$ salt/$H_2O_2$ reagent.

2. A method for synthesizing a nucleophile substituted fatty acid derivative, comprising: reacting a vinyl cyclopropyl group containing fatty acid or ester of the formula:

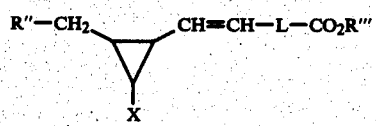

wherein R" is hydrogen, alkyl, aralkyl, or alkenyl or aralkenyl containing at least one olefinic site; L is alkylene of 3 to 9 carbon atoms, optionally containing at least one olefinic site; R''' is hydrogen, alkyl, aryl or aralkyl and X is a leaving group selected from the group consisting of chlorine, bromine, and iodine with a nucleophilic $Ag^+$ salt/$H_2O_2$ reagent.

3. The method of claim 1, wherein said leaving group X is bromine.

4. The method of claim 1, wherein said reaction is conducted at a temperature of 0° to 40° C.

5. The method of claim 1, wherein said reaction is conducted in a solvent of a dialkylether, a dialkylformamide, acetonitrile, trifluoroethanol, or dimethylsulfoxide.

6. The method of claim 2, wherein in said vinyl cyclopropyl compound reactant, said substituent R''' is methyl, R" is $CH_3(CH_2)_4CH=CH-$, X is bromine and L is $-(CH_2)_6-$.

7. The method of claim 2, wherein said group R is n-butyl, said radical -L- is $-CH_2CH=CHCH_2CH=CH(CH_2)_3-$ and R' is methyl.

8. A method for synthesizing a nucleophile substituted fatty acid derivative, comprising: reacting a vinylcyclopropyl group containing fatty acid or ester of the formula:

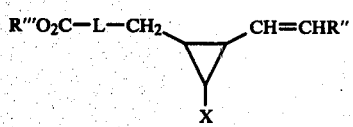

wherein R", R''', L and X are as defined above, with a nucleophilic $Ag^+$ salt/$H_2O_2$ reagent.

9. A method of synthesizing a nucleophile substituted unsaturated hydrocarbon based compound, comprising: reacting a compound of the formula:

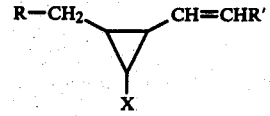

wherein R and R' independently are hydrogen, alkyl, alkenyl, cycloalkyl, cycloalkenyl, aryl, aralkyl, alkoxyalkyl or alkoxy and X is a leaving group selected from the group consisting of chlorine, bromine and iodine with a nucleophilic $Ag^+$ salt/$H_2O_2$ reagent.

* * * * *